(12) United States Patent
Garg et al.

(10) Patent No.: US 11,744,922 B2
(45) Date of Patent: Sep. 5, 2023

(54) BIOMIMETIC SPONGES FOR TISSUE REGENERATION

(71) Applicant: Saint Louis University, St. Louis, MO (US)

(72) Inventors: Koyal Garg, St. Louis, MO (US); Gabriel Haas, St. Louis, MO (US)

(73) Assignee: Saint Louis University, St. Louis, MO (US)

( * ) Notice: Subject to any disclaimer, the term of this patent is extended or adjusted under 35 U.S.C. 154(b) by 0 days.

(21) Appl. No.: 16/173,459

(22) Filed: Oct. 29, 2018

(65) Prior Publication Data

US 2019/0151513 A1 May 23, 2019

Related U.S. Application Data

(60) Provisional application No. 62/577,815, filed on Oct. 27, 2017.

(51) Int. Cl.

| | |
|---|---|
| *A61L 27/56* | (2006.01) |
| *A61L 27/58* | (2006.01) |
| *A61L 27/26* | (2006.01) |
| *A61L 27/54* | (2006.01) |
| *A61L 27/24* | (2006.01) |
| *A61L 27/22* | (2006.01) |
| *A61K 38/18* | (2006.01) |
| *A61L 27/38* | (2006.01) |
| *A61L 27/52* | (2006.01) |
| *A61L 27/32* | (2006.01) |
| *A61L 27/46* | (2006.01) |

(52) U.S. Cl.
CPC .......... *A61L 27/56* (2013.01); *A61K 38/1825* (2013.01); *A61K 38/1875* (2013.01); *A61L 27/222* (2013.01); *A61L 27/24* (2013.01); *A61L 27/3804* (2013.01); *A61L 27/54* (2013.01); *A61L 27/26* (2013.01); *A61L 27/32* (2013.01); *A61L 27/46* (2013.01); *A61L 27/52* (2013.01); *A61L 27/58* (2013.01); *A61L 2300/414* (2013.01)

(58) Field of Classification Search
None
See application file for complete search history.

(56) References Cited

U.S. PATENT DOCUMENTS

| | | | |
|---|---|---|---|
| 5,508,188 A * | 4/1996 | Barsky .................... | C12N 5/16 435/395 |
| 8,951,799 B2 * | 2/2015 | Domogatskaya .... | C12N 5/0606 435/402 |
| 9,289,533 B2 | 3/2016 | Schussler et al. | |
| 9,329,939 B2 | 5/2016 | Cho | |
| 9,629,939 B2 | 8/2017 | Flynn et al. | |
| 2004/0151705 A1 * | 8/2004 | Mizuno .................... | A61F 2/28 424/93.7 |
| 2006/0160734 A1 * | 7/2006 | Kusanagi ............... | A61K 38/39 514/9.4 |
| 2009/0143287 A1 * | 6/2009 | Ikada ...................... | A61L 27/26 514/6.9 |
| 2014/0370094 A1 * | 12/2014 | Wray ..................... | A61K 47/46 514/8.1 |
| 2015/0247126 A1 * | 9/2015 | Kidoaki ............... | C12N 5/0068 435/397 |
| 2016/0052994 A1 | 2/2016 | Sekiguchi et al. | |
| 2017/0360551 A1 * | 12/2017 | Liu .......................... | A61F 2/02 |

FOREIGN PATENT DOCUMENTS

| | | |
|---|---|---|
| WO | 2005004928 A2 | 1/2005 |
| WO | 2005004928 A2 | 2/2005 |
| WO | WO-2017036533 A1 * | 3/2017 |

OTHER PUBLICATIONS

Rohanizadeh et al.; "Gelatin sponges (Gelfoam®) as a scaffold for osteoblasts," 2008, Springer; J Mater Sci: Mater Med, vol. 19, pp. 1173-1182p (Year: 2008).*
Avitene™ Ultrafoam™ collagen hemostat, "Instructions for use" Bard, DAVOL Inc., 1998, pp. 1-4, as provided. (Year: 1998).*
Kin et al.; "Regeneration of Skeletal Muscle Using In Situ Tissue Engineering on a Acellular Collagen Sponge Scaffold in a Rabbit Model," 2007; ASAIO Journal, vol. 53, No. 4, pp. 506-513. (Year: 2007).*
Choi et al.; "Study on gelatin-containing artificial skin: I. Preparation and characteristics of novel gelatin-alginate sponge," 1999; Elsevier; Biomaterials, vol. 20, pp. 409-417. (Year: 1999).*
Ito et al.; "Adipogenesis using human adipose tissue-derived stromal cells combined with a collagen/gelatin sponge sustaining release of basic fibroblast growth factor," 2012, John Wiley & Sons; Journal of Tissue Engineering and Regenerative Medicine, vol. 8, pp. 100-1008. (Year: 2012).*
Riederer et al.; "Laminin therapy for the promotion of muscle regeneration," 2015, Elsiver; FEBS Letters, vol. 589, pp. 3449-3453. (Year: 2015).*
Rodriguez et al.; "A Preliminary Evaluation of Lyphilized Gelatin Sponges, Enhanced with Platelet-Rich Plasma, Hydroxyapatite and Chitin Whiskers for Bone Regeneration," 2013, Cells, vol. 2, pp. 244-265. (Year: 2013).*
Ito et al.; "Adipogeneisis using human adipose tissue-derived stromal cells combined with a collagen/gelatin sponge sustaining release of basic fibroblast growth factor," 2012. (Year: 2012).*
Garg et al.; "Biomimetic sponges for regeneration of skeletal muscle following trauma," 2018, Wiley; Journal of Biomedical materials Research Part A, vol. 107, No. 1, pp. 92-103. (Year: 2018).*
Hass et al.; "Biomimetic sponges improve muscle structure and function following volumetric muscle loss," Journal of Biomedical Materials Research Part A, vol. 109, No. 11, pp. 2280-2293. (Year: 2021).*

(Continued)

*Primary Examiner* — Tigabu Kassa
*Assistant Examiner* — Ivan A Greene
(74) *Attorney, Agent, or Firm* — Stock Legal, LLC; Dutro E. Campbel, II

(57) ABSTRACT

The present disclosure relates generally to tissue engineering. Disclosed herein are biomimetic sponges useful for tissue regeneration and methods for making biomimetic sponges.

19 Claims, 6 Drawing Sheets

(56) References Cited

OTHER PUBLICATIONS

Damodaran et al.; "Tethering a laminin peptide to a crosslinked collagen scaffold for biofunctionality," 2008, Wiley; Journal of Biomedical Materials Research Part A, vol. 89, No. 4, pp. 1001-1010. (Year: 2008).*

Higuchi et al.; "Biomimetic Cell Culture Proteins as Extracellular Matrices for Stem Cell Differentiation," 2012; American Chemical Society, Chemical Reviews, vol. 112, No. 8, pp. 4507-4540. (Year: 2012).*

Ghohestani et al.; "Molecular Organization of the Cutaneous Basement Membrane Zone," 2001, Elsevier; Clinics in Dermatology, vol. 19, pp. 551-562. (Year: 2001).*

Hamill et al.; "Laminins: Roles and Utility in Wound Repair," 2015, Wound Healing Society; Advances in Wound Care, vol. 4, No. 4, pp. 250-263. (Year: 2015).*

Jurga et al.; "The performance of Laminin-containing cryogel scaffolds in neural tissue regeneration," 2011, Elsevier; Biomaterials, vol. 32, No. 13, pp. 3423-3434. (Year: 2011).*

Choi et al.; "Study on gelatin-containing artificial skin: I. Preparation and characteristics of novel gelatin-alginate sponge," 1999, Elsevier; Biomaterials, vol. 20, No. 5, pp. 409-417. (Year: 1999).*

Rodriguez et al.; "A Preliminary Evaluation of Lyophilized Gelatin Sponges, Enhanced with Platelet-Rich Plasma, Hydroxyapatite and Chitin Whiskers for Bone Regeneration," 2013, Cells, vol. 2, pp. 244-265. (Year: 2013).*

Haas et al., Biomimetic sponges for regeneration of skeletal muscle following trauma. J Biomed Mater Res A, 2019, vol. 107, No. 1, pp. 92-103.

Tallawi et al., Strategies for the chemical and biological functionalization of scaffolds for cardiac tissue engineering: a review; J. R. Soc. Interface, vol. 12, 24-pages, 2015.

Shapiro et al., Novel alginate sponges for cell culture and transplantation. Biomaterials, 1997, vol. 18, No. 8, pp. 583-590.

Zhang et al., Cells behave distinctly within sponges and hydrogels due to differences of internal structure. Tissue Eng Part A, 2013. vol. 19, No. 19-20: pp. 2166-2175.

Tallawi et al., Strategies for the chemical and biological functionalization of scaffolds for cardiac tissue engineering: a review; the Royal Society Publishing, 2015, 24-pages.

Haaparanta et al., The effect of cross-linking time on a porous freeze-dried collagen scaffold using 1-ethyl-3-(3-dimethylaminopropyl)carbodiimide as a cross-linker; Journal of Applied Biomaterials & Biomechanics, 2008, vol. 6, No. 2, pp. 89-94.

Liang et al., Crosslinking structures of gelatin hydrogels crosslinked with genipin or a water-soluble carbodiimide J. Appl. Polym. Sci., 2004, vol. 91, pp. 4017-4026.

Lou et al., Swelling Behavior and Mechanical Properties of Chemically Cross-Linked Gelatin Gels for Biomedical Use; JBA Sage Publishing; 1999, 8-pages.

Rodriguez et al., A Preliminary Evaluation of Lyophilized Gelatin Sponges, Enhanced with Platelet-Rich Plasma, Hydroxyapatite and Chitin Whiskers for Bone Regeneration; Cells, 2013, pp. 244-265.

Wong et al., Effect of Crosslinking Agent Concentration on the Properties of Unmedicated Hydrogels; Pharmaceutics, 2015, vol. 7, pp. 305-319.

* cited by examiner

FIG. 1B
Gelatin (100%) | Gelatin: Collagen (90:10) | Gelatin: Collagen (70:30)
FIG. 1A 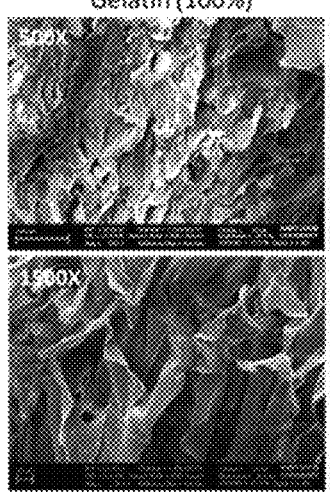 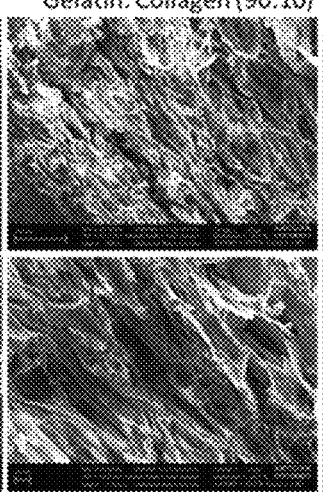 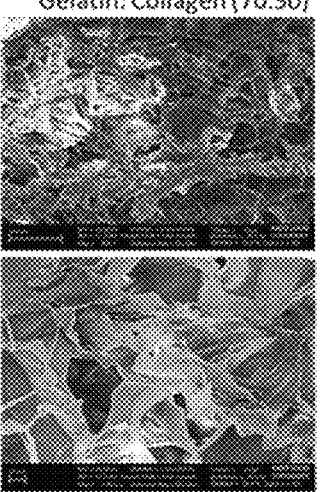 FIG. 1C
FIG. 1D FIG. 1F
FIG. 1E

BIOMIMETIC SPONGES FOR TISSUE REGENERATION

CROSS REFERENCE TO RELATED APPLICATIONS

This application claims priority to U.S. Provisional Patent Application Ser. No. 62/577,815, filed on Oct. 27, 2017, the disclosure of which is hereby incorporated by reference in its entirety.

BACKGROUND OF THE DISCLOSURE

The present disclosure relates generally to tissue engineering. More particularly, the present disclosure is directed to biomimetic sponges useful for tissue regeneration and methods for making biomimetic sponges.

A variety of method and compositions have been developed for the repair of tissue injuries and to regenerate tissues. These involve natural and synthetic materials. Supports and scaffolds provide substrates for tissue engineering and can include cells, adhesion molecules or biological agents to facilitate cellular infiltration, growth and tissue regeneration. Producing tissue engineering scaffolds has been difficult because scaffolds must possess suitable mechanical properties while also supporting cellular interaction for tissue repair and regeneration.

A clinically approved therapy for repair and regeneration of large muscle defects does not currently exist. The majority of current scaffolds are either mechanically weak or fail to enhance tissue resident stem cell activity. Accordingly, there exists a need to develop new biomimetic scaffolds and methods for preparing biomimetic scaffolds.

BRIEF DESCRIPTION OF THE DISCLOSURE

The present disclosure is generally related to tissue engineering. More particularly, the present disclosure is directed to biomimetic sponges useful for tissue regeneration and methods for making biomimetic sponges.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein:

FIGS. 1A-1F are scanning electron microscopy images of sponges taken at 500× having 100% gelatin (FIG. 1A), 90% gelatin and 10% collagen (FIG. 1B), and 70% gelatin and 30% collagen (FIG. 1C) and 1500× having 100% gelatin (FIG. 1D), 90% gelatin and 10% collagen (FIG. 1E), and 70% gelatin and 30% collagen (FIG. 1F).

DETAILED DESCRIPTION

Figure 2A:
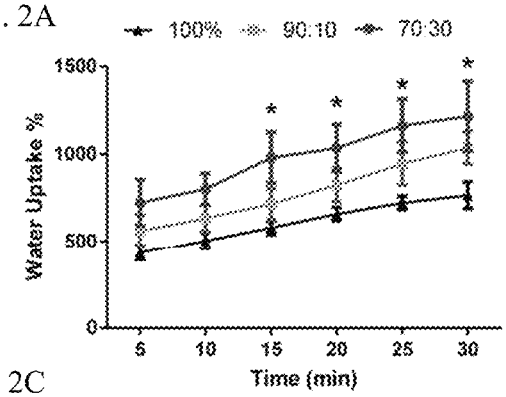
FIG. 2A depicts the water uptake percentage of biomimetic sponges.

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

As disclosed herein, the present disclosure relates to methods for making porous scaffolds that mimic the extracellular matrix (ECM) of mammalian tissues. The scaffolds contain key ECM proteins such as collagen and laminin to enhance tissue resident cell-mediated regeneration. The biomimetic sponges also possess good mechanical properties to serve as a substrate for cellular proliferation and maintain their shape and structure in injured regions of tissue. The biomimetic sponges can be fabricated in any shape or size and can be used in a number of tissue engineering applications as an acellular scaffold for skeletal muscle regeneration, bone regeneration, wound healing, stem cell expansion, drug and biomolecule delivery, and hemostasis, among others.

As used herein, "a subject in need thereof" refers to a subject having, susceptible to or at risk of a specified disease, disorder, or condition. More particularly, in the present disclosure the methods of treating tissue injury and the methods of tissue regeneration is to be used with a subset of subjects who have, are susceptible to or at elevated risk for experiencing tissue injury. Subjects may have, be susceptible to or at elevated risk for tissue injury and tissue regeneration due to family history, age, environment, and/or lifestyle. Based on the foregoing, because some of the method embodiments of the present disclosure are directed to specific subsets or subclasses of identified subjects (that is, the subset or subclass of subjects "in need" of assistance in addressing one or more specific conditions noted herein), not all subjects will fall within the subset or subclass of subjects as described herein for certain diseases, disorders or conditions.

As used herein, "susceptible" and "at risk" refer to having little resistance to a certain disease, disorder or condition, including being genetically predisposed, having a family history of, and/or having symptoms of the disease, disorder or condition.

In one aspect, the present disclosure is directed to biomimetic sponge comprising a homogeneous mixture of gelatin, collagen, and laminin. The term "homogeneous mixture" is used according to its ordinary meaning as understood by those skilled in the art to refer to a uniform mixture with no visible phase separation of the components making up the solution.

The biomimetic sponge can further include a cross-linker. Suitable cross-linkers include N-(3-Dimethylaminopropyl)-N'-ethylcarbodiimide (EDC), genipin and glutaraldehyde, for example.

The biomimetic sponge can further include at least one of a biomolecule, a drug, and a cell. Suitable biomolecules include proteins, polypeptides, peptide fragments, and amino acids, for example. Suitable proteins, polypeptides, and peptide fragments include isolated, purified, synthesized, and recombinant forms. Suitable drugs include anti-inflammatory drugs, immunosuppressant drugs, cytokines, chemokines, growth factors, and combinations thereof. Any desired cell can suitably be incorporated into biomimetic sponges. Suitable cells include stem cells, muscle cells, fibroblasts, and osteoblasts, for example.

The biomimetic sponge can include a degradation rate of at least 2 weeks in vitro.

The biomimetic sponge can have a gelatin to collagen ratio ranging from about 99 weight % (wt. %) gelatin to about 1 wt. % collagen to about 70 wt. % gelatin to about 30 wt. % collagen.

Suitable amounts of laminin can range from about 62.5 nM to about 250 nM.

The biomimetic sponge can have a peak load ranging from about 0.001 kN to about 0.1 kN. Peak load can be determined by compression strength testing.

The biomimetic sponge can have a peak stress ranging from about 4 MPa to about 350 MPa. Peak stress can be determined by compression strength testing.

The biomimetic sponge can have a compressive modulus ranging from about 20 kPa to about 1050 MPa. Compressive modulus can be measured by compression strength testing.

The biomimetic sponge can have a water uptake percentage ranging from about 14%/minute to about 20%/minute.

In another aspect, the present disclosure is directed to a method of preparing a biomimetic sponge, the method comprising: providing a gelatin precursor solution; introducing the gelatin precursor solution into a mold; adding a collagen solution to the gelatin precursor solution; adding laminin to the gelatin precursor solution; placing the mold into a methanol bath; allowing the gelatin precursor solution in the mold to gel at a desired temperature and time to form a gel; incubating the gel at a second desired temperature to prepare a frozen gel; incubating the frozen gel at a third desired temperature; and drying the frozen gel.

In one embodiment, the gelatin precursor solution, the collagen solution and laminin are mixed to produce a homogeneous mixture. As used herein, "homogeneous mixture" refers to a solution having a uniform composition and properties; a mixture that is uniform throughout. The homogeneous mixture of gelatin, collagen and laminin can be made using any mixing method known to one skilled in the art including, for example, vortexing, pipetting, stirring, shaking, and combinations thereof.

The method can further include adding a cross-linker to the gelatin precursor solution. Suitable cross-linkers include those described herein.

The method can further include adding at least one of a biomolecule and a drug to the gelatin precursor solution. Suitable biomolecules and drugs are described herein. Adding a biomolecule and/or a drug to the gelatin precursor solution results in the biomolecule and/or a drug being encapsulated in the resulting biomimetic sponge.

The method can further include culturing a cell in the presence of a biomimetic sponge under suitable conditions that permit cells to migrate into the biomimetic sponge and populate the biomimetic sponge. Cells in the biomimetic sponge can further migrate within the biomimetic sponge, grow within the biomimetic sponge, proliferate within the biomimetic sponge and secrete molecules from within the biomimetic sponges.

The ratio of gelatin to collagen can range from about 99 wt. % gelatin to about 1 wt. % collagen to about 70 wt. % gelatin to about 30 wt. % collagen.

Suitable amounts of laminin can range from about 62.5 nM to about 250 nM.

In another aspect, the present disclosure is directed to a method for treating a tissue injury in a subject in need thereof, the method comprising: providing a biomimetic sponge that comprises a homogeneous mixture of gelatin, collage, and laminin; placing the biomimetic sponge in a region of tissue injury in the subject in need thereof.

The tissue injury can be a soft tissue injury. The tissue injury can be a bone injury. The soft tissue injury comprises a skin injury, a muscle injury, brun wounds, and lesions, for example.

The biomimetic sponge can further include a cross-linker as described herein.

The biomimetic sponge can further include biomolecules, drugs, and cells, as described herein.

In another aspect, the present disclosure is directed to a method for sustained delivery of a molecule, the method comprising: providing a biomimetic sponge that comprises a homogeneous mixture of gelatin, collage, and laminin; and at least one molecule.

Suitable molecules include biomolecules and drugs, as described herein.

EXAMPLES

Example 1

In this Example, biomimetic sponges were fabricated.

A 3 wt. % porcine skin gelatin (Sigma-Aldrich) solution was prepared in DI water heated to 60° C. After the gelatin had completely dissolved, the solution was allowed to cool to 50° C., and EDC (20 mM) was added. The solution was then vortexed vigorously and added to square plastic molds with 3 mg/mL rat tail collagen I (Gibco) solution in gelatin:collagen ratios of 100:0 (pure gelatin), 90:10, and 70:30. LM-111 (Trevigen) was then added to the molds at a final concentration of 50 μg/mL and mixed thoroughly by pipetting the solution in the molds up and down. The molds were placed in a 100% methanol bath, and allowed to gel at 4° C. for 30 minutes, followed by overnight freezing at −8° C. The molds were then moved to a −80° C. freezer for 24 hours. Then the methanol was removed and they were frozen for another 24 hours at −80° C. The frozen molds were lyophilized for at least 19 hours. The cross-sections of the lyophilized sponges were observed through scanning electron microscopy (SEM) (see, FIGS. 1A-1F). The addition of collagen increased the overall porous structure and void space in the sponges.

Example 2

In this Example, water uptake percentage of the biomimetic sponges was determined.

Water uptake percentage was calculated by measuring the dry and hydrated weight of each sponge (n=3) at five-minute time intervals after soaking each sponge in 1 mL of water. Formula (I) was used to calculate water uptake percentage:

$$\text{Water Uptake Percentage} = \frac{(\text{Hydrated Weight} - \text{Dry Weight})}{\text{Dry Weight}} \times 100\% \quad (I)$$

The increase in the porous structure also resulted in enhanced water absorption capacity (FIG. 2A). The water uptake capacity was 766% for pure gelatin, 1037% for 90:10 and 1216% for 70:30 sponges. The 70:30 sponges showed the highest water uptake capacity, indicating a highly porous three-dimensional (3D) structure.

Example 3

In this Example, compression testing of the biomimetic sponges was performed.

Figure 2B:
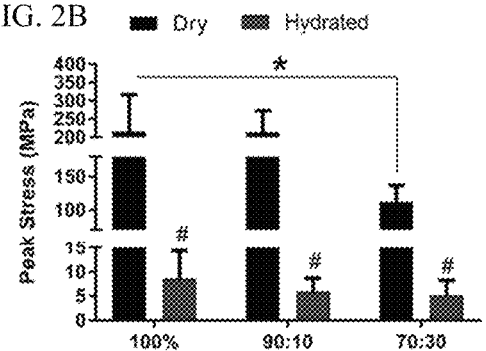
FIGS. 2B-2D depict the peak stress (FIG. 2B), the peak load (FIG. 2C) and compressive modulus (FIG. 2D) of dry and hydrated biomimetic sponges.
Figure 2C:
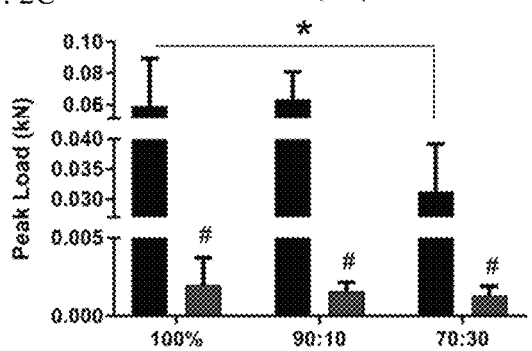
Figure 2D:
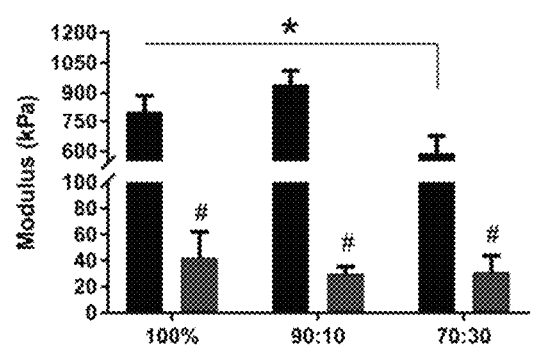

Compression testing was performed using a MTS Criterion Model 42. The sponges (n=4) were first tested while dry, and then tested again after being hydrated in 3 mL of DI water for 5 minutes. A strain rate of 10 mm/min was used until a strain percentage of 50% was reached. The peak stress, peak load, compressive modulus values were obtained from MTS software (MTS TestSuite: TW Elite) using the stress-strain curve. The results of the compression testing are shown in FIG. 2B-2D. The peak load of the gelatin sponges was determined to be 60N. This value is ~80 times the reported peak load value of gelatin sponges (~0.75N) that contained 50 mM EDC prior to refrigeration. The compressive modulus of the pure gelatin sponge was determined to be 808 kPa. This is ~5 times higher than the compressive modulus of the commercially available hemostatic gelatin sponge, Spongostan (Ferrosan Medical Device, MS0003). Addition of 30% collagen significantly lowered the compressive modulus, peak load and peak stress compared to the gelatin control sponge. Overall, the hydrated sponges showed a significant drop in the peak stress, peak load and compressive modulus. The hydrated values were closer to the Young's modulus of the native skeletal muscle reported in previous studies (~10 kPa).

Example 4

In this Example, myoblasts were cultured with the biomimetic sponges.

Figure 3:
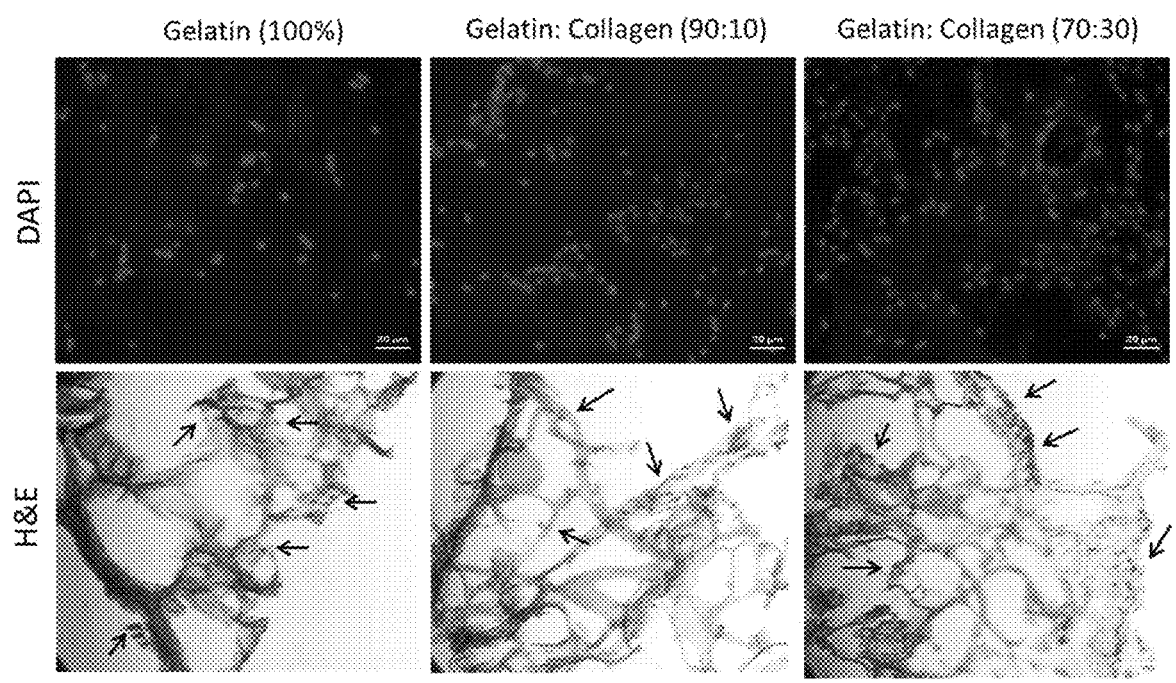
FIG. 3 depicts cryosections of sponges stained with DAPI (top panel) and H&E (bottom panel). The biomimetic sponges showed the greatest myoblast infiltration into their three-dimensional structure.

The sponges were disinfected in 95% ethanol for 5 minutes, rinsed twice in 1× phosphate buffer solution (PBS) for 5 minutes each, followed by overnight incubation in growth media (DMEM-F12 containing 10% fetal bovine serum (FBS), 10% horse serum (HS), and 1% penicillin-streptomycin). $C_2C_{12}$ myoblasts were seeded on the sponges at a density of 500,000 cells/well in 12 well plate for 5 days (n=3-4) in the growth media. The sponges were removed from cell culture media on day 5 of culture, immersed in optimal cutting temperature (OCT) compound and frozen in liquid nitrogen. Cross-sections of the 30 μm thickness were stained with DAPI and hematoxylin and eosin (H&E). Images were captured at 40× magnification using a Zeiss Axiocam microscope. The cryosections of the cell-seeded biomimetic sponges were obtained on day 5. The sections stained with DAPI and H&E are shown in FIG. 3. The number of cellular nuclei increased with increasing percentage of collagen in the sponges. The 70:30 sponges showed the highest infiltration of myoblasts into their 3D structure. The H&E images show the location of cellular nuclei with respect to the scaffold. The $C_2C_{12}$ myoblasts were observed to line the pores of the sponges. Similar to the DAPI stained images, the cellular quantity and overall infiltration increased with increasing concentrations of collagen.

Figure 4A:
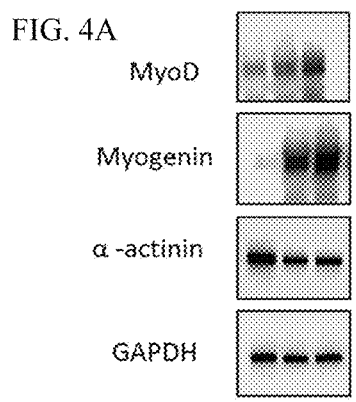
FIGS. 4A-4D depict myogenic protein expression analyzed by Western blot analysis (FIG. 4A) and quantitation of MyoD (FIG. 4B), myogenin (FIG. 4C) and α-actinin (FIG. 4D) with respect to GAPDH for days 1 and 5.
Figure 4B:
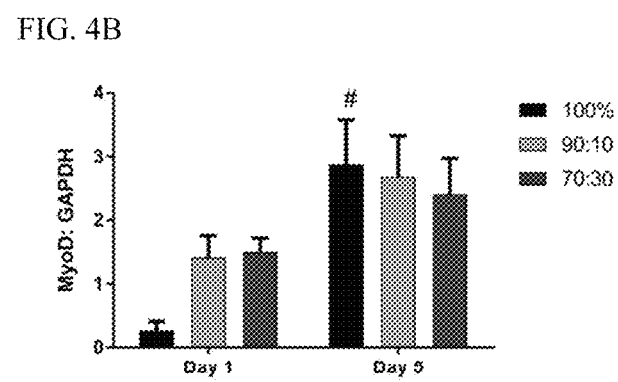
Figure 4C:
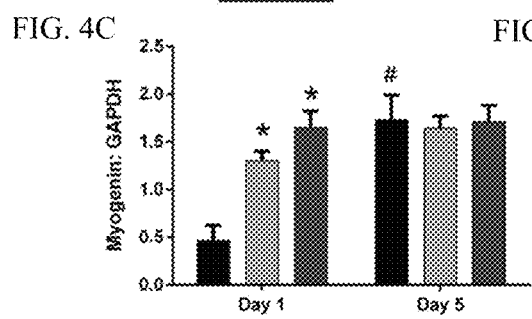
Figure 4D:
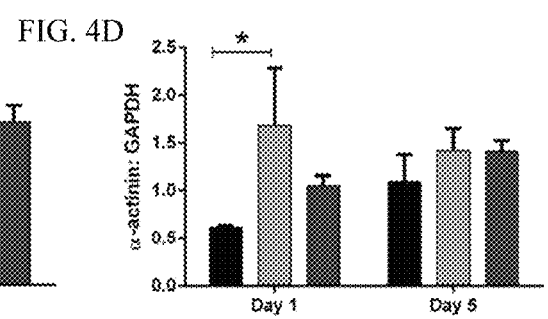

Myogenic protein expression by myoblasts cultured in sponges was then determined. Protein lysates from myoblasts were collected on days 1 and 5 and were quantified for myogenic markers using western blotting as previously described. Briefly, the sponges were rinsed twice in PBS and the cellular protein lysates were collected in RIPA buffer with protease inhibitor cocktail (Sigma). The protein concentration was determined with BSA reference standards. Samples consisting of 30 μL of denatured protein and 10 μL of Laemmli buffer were resolved by SDS-polyacrylamide gel electrophoresis (SDS-PAGE) using 4-20% gels (Bio-Rad) and transferred onto nitrocellulose membranes. Equal protein loading was verified by Ponceau S staining of the membranes. The membranes were probed using anti-desmin (Abcam), anti-MyoD (Thermo Fisher Scientific), anti-myogenin (Millipore), anti-GAPDH (Cell Signalling), anti-α-actinin (Cell Signaling), and HRP-conjugated secondary antibodies. The expression of myogenic proteins in $C_2C_{12}$ myoblasts cultured on the sponges is presented in FIG. 4A. The expression of MyoD trended higher on the 90:10 and 70:30 sponges compared to pure gelatin sponge on day 1. On day 5, MyoD expression significantly increased on the gelatin sponge compared to day 1 but was not significantly different between the sponges. The expression of myogenin showed a linear increase with increasing collagen concentration in the sponges and was significantly higher in the 90:10 and 70:30 sponges compared to pure gelatin. No significant differences were observed in the expression of myogenin between sponges on day 5. However, a significant increase in myogenin expression was observed on the pure gelatin sponge on day 5 compared to day 1. The expression of α-actinin (FIG. 4D) was significantly higher on the 90:10 biomimetic sponge compared to pure gelatin sponge on day 1 but no significant differences were observed on day 5 between the sponges.

Example 5

In this Example, myokine secretion by myoblasts was determined.

Figure 5:
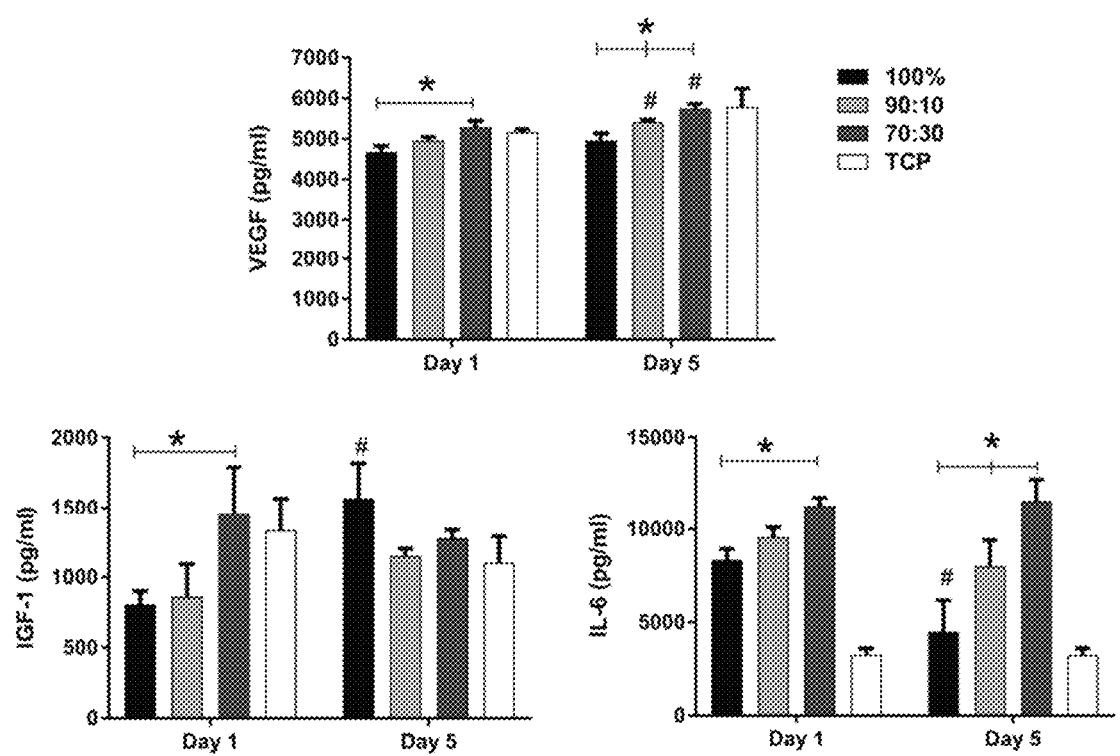
FIG. 5 depicts the quantification of VEGF, IL-6 and IGF-1 levels produced by myoblasts cultured on the sponges. The 70:30 biomimetic sponges resulted in the highest levels of VEGF and IL-6 production on days 1 and 5. The levels of IGF-1 were significantly higher on day 1.

Cell culture supernatants were collected on day 1 and 5. The production of vascular endothelial growth factor (VEGF), interleukin-6 (IL-6), and insulin-like growth factor (IGF)-1 by $C_2C_{12}$ myoblasts was quantified in cell-culture supernatants using ELISA (Peprotech) as per manufacturer's instructions. The ELISA results for VEGF, IL-6 and IGF-1 in cell-culture supernatants are shown in FIG. 5. The levels of VEGF and IL-6 released by $C_2C_{12}$ myoblasts increased linearly with increasing percentage of collagen in the biomimetic sponges. The myoblasts cultured on the 70:30 sponges produced the highest quantity of VEGF and IL-6 compared to 100% gelatin sponges at both day 1 and 5. The quantity of IGF-1 secreted by myoblasts was significantly increased on 70:30 sponges compared to 100% gelatin sponges at day 1. The quantity of released VEGF was significantly increased on the 90:10 and 70:30 sponges at day 5 compared to day 1 but remained constant on the 100% gelatin sponges. The level of IL-6 was decreased but that of IGF-1 was increased on the 100% gelatin sponges at day 5 of culture.

Example 6

In this Example, encapsulation of FK-506 in the biomimetic sponges was determined.

Figure 6:
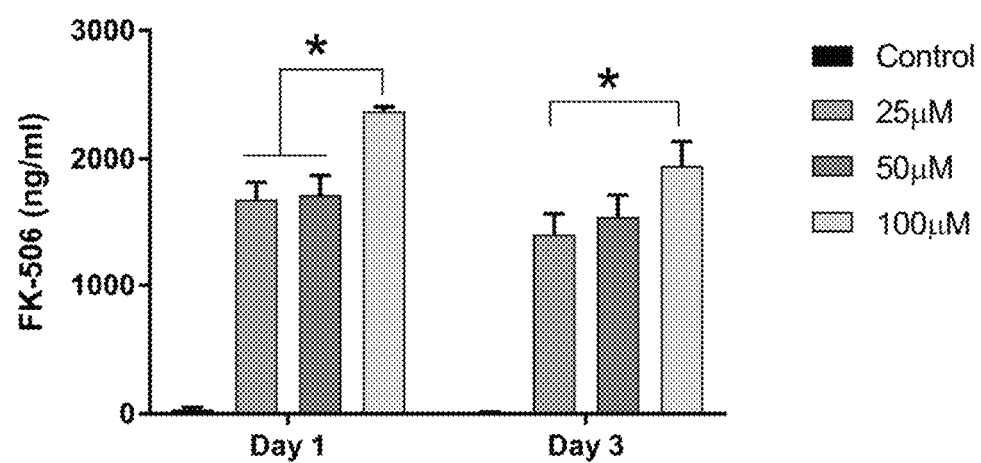
FIG. 6 depicts the quantification of FK-506 released from the 70:30 biomimetic sponges on days 1 and 3.

The fungal macrolide FK-506 (Tacrolimus) is a FDA-approved immunosuppressant. FK-506 was encapsulated in 70:30 biomimetic sponges at final concentrations of 25, 50 and 100 μM. The sponges were incubated at 37° C. for 3 days in cell culture medium and the levels of FK-506 released were quantified using an ELISA (Novus Biologicals). The results are shown in FIG. 6. The sponges showed a dose-dependent release of FK-506. The levels released from the sponges containing 100 μM of FK-506 were significantly higher than those containing 20 or 50 µM on day 1. By day 3, the FK-506 levels released from the sponge containing 100 µM were significantly higher than from sponges containing 25 µM.

Clinically approved therapies for repair and regeneration of large tissue defects such as muscle defects do not currently exist. The majority of current scaffolds are either mechanically weak or fail to enhance tissue resident stem cell activity. The biomimetic sponges of the present disclosure provide several advantages over current technology. The biomimetic sponges of the present disclosure contain a mixture of pro-regenerative proteins such as collagen and laminin. The biomimetic sponges of the present disclosure also contain gelatin that enhances the mechanical properties and durability of the biomimetic sponges while retaining biocompatibility. Biomolecules and/or drugs can be readily incorporated into the biomimetic sponges of the present disclosure. The biomimetic sponges of the present disclosure can be fabricated in a variety of shapes and sizes to provide a readily adaptable solution to a variety of wounds and tissue defects. The biomimetic sponges of the present disclosure can also be fabricated in a short-time frame without using specialized lab equipment.

In view of the above, it will be seen that the several advantages of the disclosure are achieved and other advantageous results attained. As various changes could be made in the above methods without departing from the scope of the disclosure, it is intended that all matter contained in the above description and shown in the accompanying drawings shall be interpreted as illustrative and not in a limiting sense.

When introducing elements of the present disclosure or the various versions, embodiment(s) or aspects thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. A biomimetic sponge comprising a homogenous mixture of gelatin, collagen, and laminin-111 crosslinked with 1-ethyl-3-(3-dimethyl aminopropyl) carbodiimide, wherein the ratio of gelatin to collagen ranges from about 99 wt. % gelatin to about 1 wt. % collagen to about 96 wt. % gelatin to about 4 wt. % collagen, the amount of laminin ranges from about 0.04 wt. % to about 2 wt. %, and the crosslinking results in a degradation rate ranging from about 2 weeks to about 4 weeks.

2. The biomimetic sponge of claim 1 further comprising at least one of a biomolecule, a drug and a cell.

3. The biomimetic sponge of claim 1 wherein the crosslinking results in a peak load ranging from about 0.001 kN to about 0.1 kN.

4. The biomimetic sponge of claim 1 further comprising wherein the crosslinking results in a peak stress ranging from about 4 MPa to about 350 MPa.

5. The biomimetic sponge of claim 1 further comprising wherein the crosslinking results in a peak stress ranging from about 4 MPa to about 15 MPa wherein the biomimetic sponge is hydrated.

6. The biomimetic sponge of claim 1 further comprising wherein the crosslinking results in a peak stress ranging from about 380 kPa to about 1100 kPa.

7. The biomimetic sponge of claim 1 further comprising wherein the crosslinking results in a water uptake percentage ranging from about 14%/minute to about 20%/minute.

8. A method of preparing a biomimetic sponge, the method comprising the steps of:

providing a homogenous mixture of gelatin, collagen, and laminin-111, wherein the ratio of gelatin to collagen ranges from about 99 wt. % gelatin to about 1 wt. % collagen to about 96 wt. % gelatin to about 4 wt. % collagen and the amount of laminin ranges from about 0.04 wt. % to about 2 wt. %; and crosslinking the homogenous mixture with 1-ethyl-3-(3-dimethyl aminopropyl) carbodiimide, wherein the crosslinking results in a degradation rate ranging from about 2 weeks to about 4 weeks.

9. The method of claim 8 further comprising adding at least one of a biomolecule and a drug to the homogenous mixture.

10. The method of claim 8 further comprising rehydrating the biomimetic sponge.

11. The method of claim 8 further comprising contacting a cell with the biomimetic sponge.

12. A method of treating a tissue injury in a subject in need thereof, the method comprising the steps of:

providing a biomimetic sponge that comprises a homogenous mixture of gelatin, collagen, and laminin-111 crosslinked with 1-ethyl-3-(3-dimethyl aminopropyl) carbodiimide, wherein the ratio of gelatin to collagen ranges from about 99 wt. % gelatin to about 1 wt. % collagen to about 96 wt. % gelatin to about 4 wt. % collagen, the amount of laminin ranges from about 0.04 wt. % to about 2 wt, %, and the crosslinking results in a degradation rate ranging from about 2 weeks to about 4 weeks and placing the biomimetic sponge in a region of tissue injury in the subject in need thereof.

13. The method of claim 12 wherein the tissue injury comprises a soft tissue injury.

14. The method of claim 13 wherein the soft tissue injury comprises a skin injury, a muscle injury, a burn wound, a lesion, and combinations thereof.

15. The method of claim 12 wherein the tissue injury comprises a bone injury.

16. The biomimetic sponge of claim 1, wherein the content of gelatin ranges from about 96 wt. % to about 99 wt. %.

17. The biomimetic sponge of claim 1, wherein the homogenous mixture is crosslinked with about 20 mM of 1-ethyl-3-(3-dimethyl aminopropyl) carbodiimide.

18. A biomimetic sponge comprising a homogeneous mixture of gelatin, collagen, and laminin-111, crosslinked with 1-ethyl-3-(3-dimethyl aminopropyl) carbodiimide, wherein the ratio of gelatin to collagen ranges from about 99 wt. % gelatin to about 1 wt. % collagen to about 96 wt. % gelatin to about 4 wt. % collagen, the amount of laminin ranges from about 0.04 wt. % to about 2 wt. %, and the crosslinking results in a degradation rate ranging from about 2 weeks to about 4 weeks, produced by providing a homogenous mixture of gelatin, collagen, and laminin, crosslinking the homogenous mixture with 1-ethyl-3-(3-dimethyl aminopropyl) carbodiimide; freezing the homogenous mixture; and drying the frozen homogenous mixture to form the biomimetic sponge.

19. The biomimetic sponge of claim 18, wherein the homogenous mixture is crosslinked with about 20 mM of 1-ethyl-3-(3-dimethyl aminopropyl) carbodiimide.

* * * * *